United States Patent
Timm

(10) Patent No.: US 7,494,487 B2
(45) Date of Patent: Feb. 24, 2009

(54) APPARATUS AND METHOD FOR APPLICATION OF A PHARMACEUTICAL TO THE TYMPANIC MEMBRANE FOR PHOTODYNAMIC LASER MYRINGOTOMY

(75) Inventor: Edward J. Timm, Cumming, GA (US)

(73) Assignee: Mobius Therapeutics, LLC, St. Louis, MO (US)

( * ) Notice: Subject to any disclaimer, the term of this patent is extended or adjusted under 35 U.S.C. 154(b) by 180 days.

(21) Appl. No.: 11/556,578

(22) Filed: Nov. 3, 2006

(65) Prior Publication Data

US 2008/0108936 A1     May 8, 2008

(51) Int. Cl.
*A61M 31/00* (2006.01)
*A61M 25/00* (2006.01)
*A61M 5/00* (2006.01)

(52) U.S. Cl. .................... 604/514; 604/264
(58) Field of Classification Search ............. 604/21, 604/275, 523, 272, 514
See application file for complete search history.

(56) References Cited

U.S. PATENT DOCUMENTS 3,650,393 A * 3/1972 Reiss et al. ............ 206/366
5,385,738 A * 1/1995 Yamahira et al. ........... 424/489
5,954,682 A * 9/1999 Petrus ........................... 604/1
6,358,231 B1 * 3/2002 Schindler et al. .............. 604/1

OTHER PUBLICATIONS

D'Eredita, Riccardo. "Contact Diode laser myringotomy and mitomycin C in children" online Jun. 9, 2004. Otoaryngology Head and Neck Surgery 2004; 130: 742-6.*

* cited by examiner

*Primary Examiner*—Kevin C Sirmons
*Assistant Examiner*—Elizabeth R MacNeill
(74) *Attorney, Agent, or Firm*—Thompson Coburn LLP

(57) ABSTRACT

A packaged kit for performing a photodynamic laser myringotomy includes a plurality of ear needles having different shaped absorbent applicators on distal ends of the needles, a vial of a single dose of an otologic formulation of mitomycin-C, a diluent carrier containing sterilized water, and a syringe. The component parts of the kit are used together to reconstitute the contents of the vial with the water in the diluent carrier, and then draw the reconstituted drug into the syringe. A selected one of the plurality of ear needles is then communicated with the syringe. The syringe and needle are then used to inject the reconstituted drug into the absorbent pad at the end of the needle, and the absorbent pad containing the drug is used to apply the drug to the tympanic membrane. The application of the drug to the tympanic membrane prepares the membrane for a myringotomy procedure, and in particular, a photodynamic laser myringotomy.

19 Claims, 4 Drawing Sheets

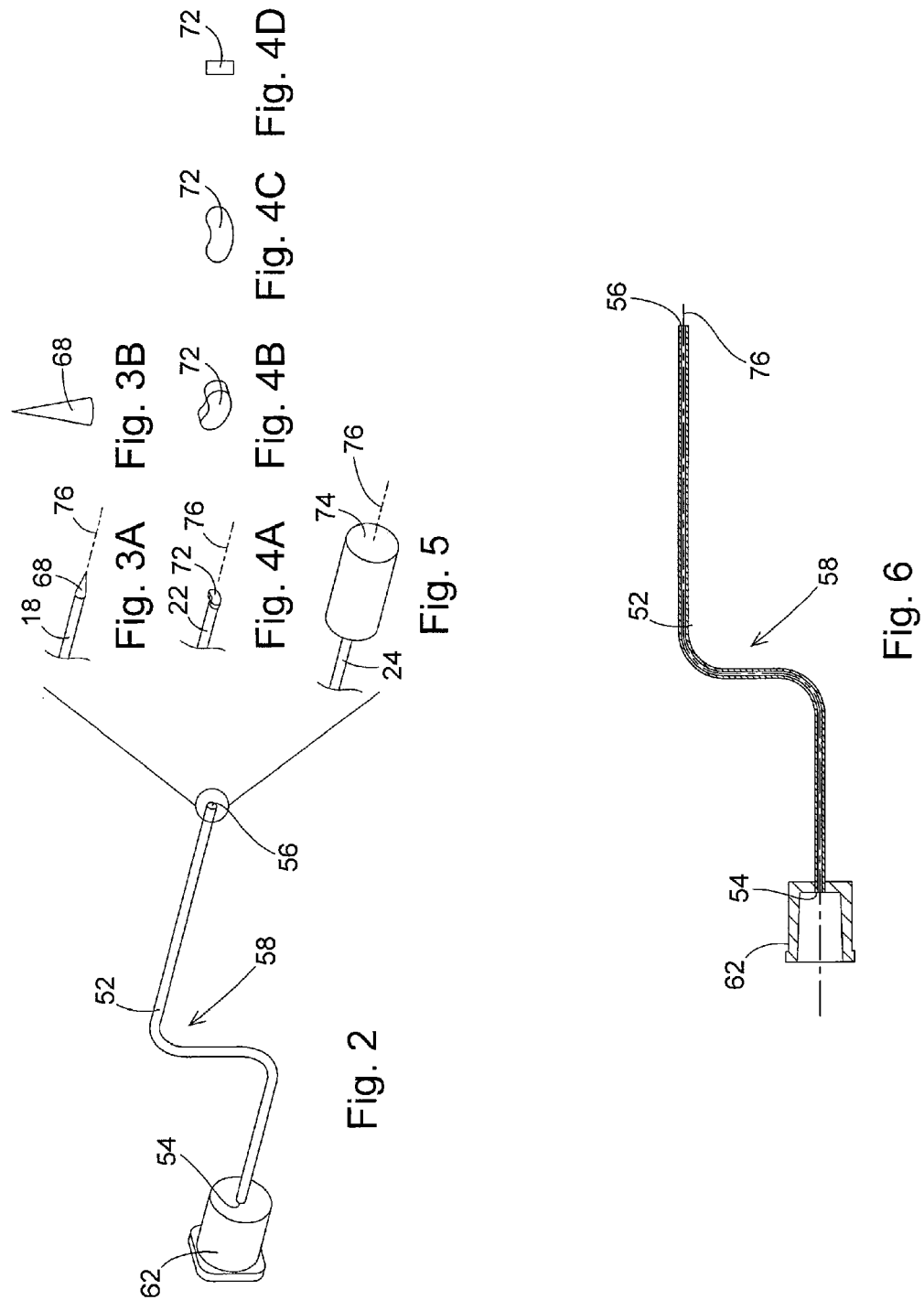

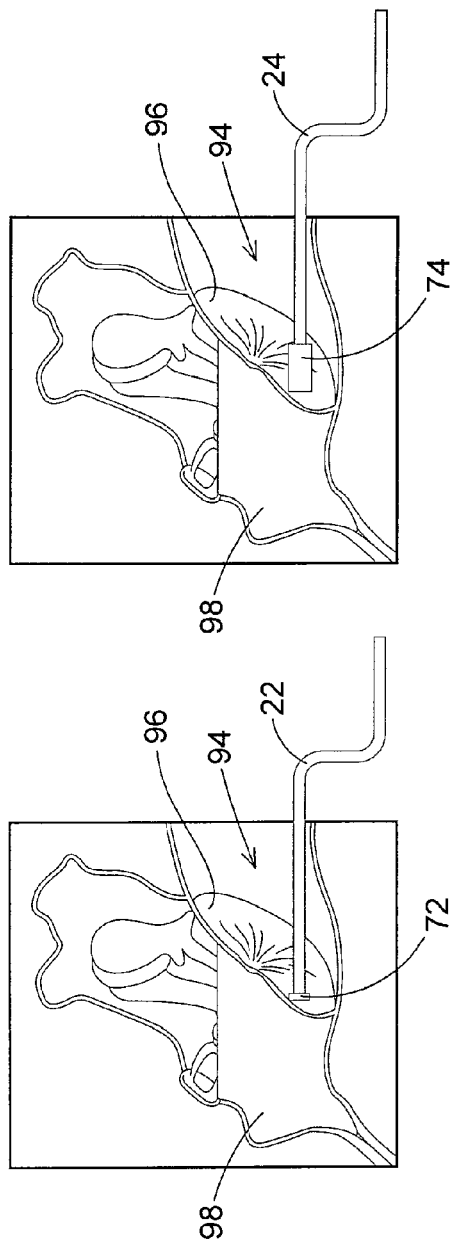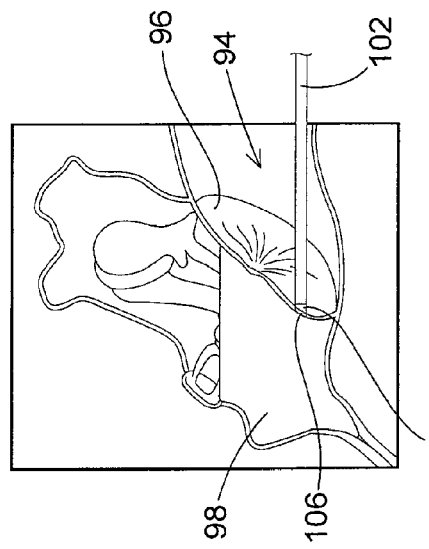

APPARATUS AND METHOD FOR APPLICATION OF A PHARMACEUTICAL TO THE TYMPANIC MEMBRANE FOR PHOTODYNAMIC LASER MYRINGOTOMY

BACKGROUND OF THE INVENTION

1. Field of the Invention

The present invention pertains to an apparatus and method for applying a pharmaceutical to the tympanic membrane in preparation for performing a photodynamic laser myringotomy. In particular, the present invention pertains to a packaged kit that includes a plurality of ear needles having different shaped absorbent applicators on distal ends of the needles, a vial of a single dose of an otologic formulation of mitomycin-C, a diluent carrier containing sterilized water, and a syringe. The component parts of the apparatus are used together to reconstitute the contents of the vial with the water in the diluent carrier, and then draw the reconstituted drug into the syringe. A selected one of the plurality of ear needles is then communicated with the syringe. The syringe and needle are then used to inject the reconstituted drug into the absorbent pad at the end of the needle, and use the absorbent pad containing the drug to apply the drug to the tympanic membrane. The application of the drug to the tympanic membrane prepares the membrane for a myringotomy procedure, and in particular, a photodynamic laser myringotomy.

2. Description of the Related Art

A myringotomy, which is a surgical puncture of the ear tympanic membrane or ear drum, is the most often performed procedure for relieving recurrent acute otitis media (RAOM), or recurrent ear infections resulting from fluid build-up in the middle ear. Recurrent acute otitis media is the most common reason for children's visits to physicians and results in more than 600,000 myringotomy procedures annually in the United States alone. Myringotomy is the single-most common surgical procedure performed on patients under the age of 15.

However, myringotomy alone often will not result in the sustained relief of the infection. In order to relieve the infection, the opening in the ear drum that allows for the fluid drainage must remain open for an extended period of time. This allows for ventilation of the ear canal and the resolution of the infection. The myringotomy opening through the ear drum is kept open by the implantation of a pressure equalization tube in the ear drum. The insertion of the tube through the ear drum allows drainage of the fluid in the middle ear that is the source of the ear infection. The ear tube is typically a small plastic tube having a spool shape. While this is not a perfect solution, inserting the pressure equalization tube through the ear drum most often achieves the desired clinical objective, the resolution of the infection.

The tube insertion is a routine procedure, and typically requires only a few minutes of the physician's time. The tube insertion can be performed as an outpatient surgery. However, because the procedure is typically performed on a child, it is often necessary that the child be unconscious or under a general anesthesia in order to achieve the desired level of compliance from the child. The need to anesthetize the child transforms what would be a very simple clinical procedure into a fully involved surgical procedure. It would be very desirable to remove the anesthesia requirement from the myringotomy procedure. With the removal of the anesthesia requirement, a myringotomy procedure could be performed by the physician at most any convenient location.

Myringotomies have been performed without the use of pressure equalization tubes. In these investigational myringotomy procedures, the physician uses a lance to produce an opening in the ear drum and also uses mitomycin-C to treat the ear drum in the area of the lance insertion. Mitomycin-C is an anti-metabolic agent that acts by interrupting DNA synthesis. It has been used as a chemotherapy agent, for example, in stomach and pancreatic cancers, for many years. Its anti-metabolic properties have prompted ophthalmologists to consider its use as a means of improving patency in trabeculectomy surgery. This procedure is well suited for the use of mitomycin, and the use of mitomycin in the procedure has ultimately become a standard of physicians.

The successful fistulae formation in glaucoma surgery with the accompanying use of mitomycin-C has resulted in experimentation in a variety of different surgical procedures where the desired end point, a functional, patent fistulae, is the same. Most notable among these procedures is the myringotomy procedure, or the surgical creation of a pathway through the tympanic membrane.

A myringotomy performed with a lance and the concomitant use of mitomycin-C has been demonstrated to provide a statistically significant increase in the time required for closure of the fistulae formed, versus a myringotomy procedure performed without the benefit of the accompanying use of mitomycin-C. It has been further demonstrated that the use of post-operative dexamethasone or an equivalent anti-inflammatory agent has further improved these results, providing data functionally equivalent to that of a myringotomy procedure performed with pressure equalization tube insertion.

The use of a laser for performance of a myringotomy procedure is also well understood. However, the use of a laser alone in the procedure is generally viewed as inefficient in the treatment of recurrent acute otitis media, or ear infections due to fluid build-up in the middle ear, because the laser opening in the ear drum will not remain open long enough to achieve the desired clinical end point.

While the procedures discussed above eliminate the use of the pressure equalization tubes typically employed in myringotomy procedures, they do not address the critical issue of patient compliance and the resultant need for anesthesia when performing a myringotomy procedure on a child.

SUMMARY OF THE INVENTION

Mitomycin-C in its natural state is purple in color. It has been envisioned by the inventor that the application of mitomycin-C to the tympanic membrane or ear drum in the middle ear would give the membrane the purple color of the mitomycin-C. Furthermore, suspending the mitomycin-C on the tympanic membrane with a viscous agent and/or an adhesive agent mixed with the mitomycin-C would cause the site of application of the mitomycin-C on the ear drum to bear the unique purple color of the mitomycin-C. With the specific colored mitomycin-C in place on the tympanic membrane, a laser tuned to the specific color of the mitomycin-C applied to the tympanic membrane could be used to produce a photodynamic, selective, laser myringotomy, i.e., a pressure equalization opening through the ear drum. The effects of the mitomycin-C applied to the ear drum would sustain the opening for an extended period of time, while the non-invasive nature of the laser beam used in producing the opening through the ear drum would accommodate the non-compliant child patient population.

Thus, the present invention provides an apparatus and method for the application of a single dose of an otologic formulation of mitomycin-C to the ear drum of a patient, where the mitomycin-C is suspended on the ear drum by a viscous agent and/or an adhesive agent and bears a specific color.

Furthermore, the apparatus and method of the invention make use of a laser that is specifically tuned to the color of the mitomycin-C applied to the ear drum. The laser beam emitted by the specifically tuned laser forms an incision or opening through the ear drum at the location treated by the mitomycin-C.

Still further, the apparatus and method of the invention employs a packaged kit that includes a vial of the mitomycin-C, a syringe, a diluent carrier, and a plurality of ear needles with each needle having a different-shaped absorbent pad at the needle distal end. The diluent carrier is used to extract the mitomycin-C from the vial and mix the mitomycin-C with water, forming a single dose of an otologic formulation of the mitomycin-C. The syringe extracts the single dose of mitomycin-C from the diluent carrier, and a selected one of the plurality of ear needles is used with the syringe to apply the mitomycin-C to the surface of the tympanic membrane. The laser beam tuned to the specific color of the mitomycin-C applied to the tympanic membrane is then used to form the opening through the ear drum. The mitomycin-C applied to the ear drum causes the opening formed to remain open for sufficient time to allow drainage of the fluid in the ear and the resolution of the infection caused by the presence of the fluid.

The apparatus of the invention and its method of use discussed above enable a safe and simplified photodynamic laser myringotomy procedure that is non-invasive and accommodates the non-compliant child patient population.

DESCRIPTION OF THE DRAWING FIGS.

Further features of the invention are set forth in the following detailed description of the preferred embodiment of the invention and in the application drawing figures.

FIG. 2 is a perspective view of one of the ear needles of the apparatus.

FIGS. 3a and 3b are views of a cone-shaped absorbent pad fixed on the distal end of one of the ear needles.

FIGS. 4a-d are views of a planar, kidney-shaped absorbent pad fixed on the distal end of one of the ear needles.

FIG. 5 is a view of a cylinder-shaped absorbent pad fixed on the distal end of one of the ear needles.

FIG. 6 is a side-sectioned view of one of the ear needles with the absorbent pad removed from the distal end.

Figure 7:
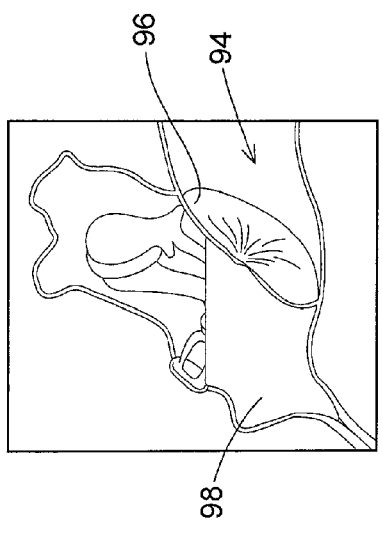

FIG. 7 is a sectioned representation of an inner ear canal.

Figure 8:
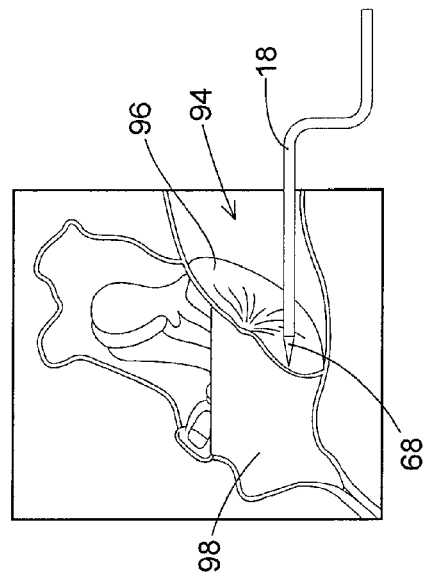

FIG. 8 is a representation of a portion of the inner ear canal shown in the rectangle of FIG. 7.

Figure 9:
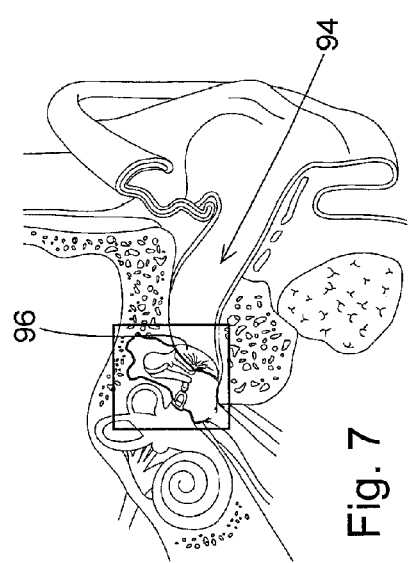

FIG. 9 is a view similar to FIG. 8, but showing a pharmaceutical being applied to the ear drum by one of the plurality of ear needles of the apparatus.

FIG. 10 is a view similar to FIG. 9, but showing the pharmaceutical being applied by another of the ear needles of the apparatus.

FIG. 11 is a view similar to FIG. 9, but showing the pharmaceutical being applied by another of the ear needles of the apparatus.

FIG. 12 is a view similar to FIG. 9, but showing a laser beam ablating the tympanic membrane at a location treated by the pharmaceutical of the apparatus.

DETAILED DESCRIPTION OF THE PREFERRED EMBODIMENT OF THE INVENTION

Figure 1:
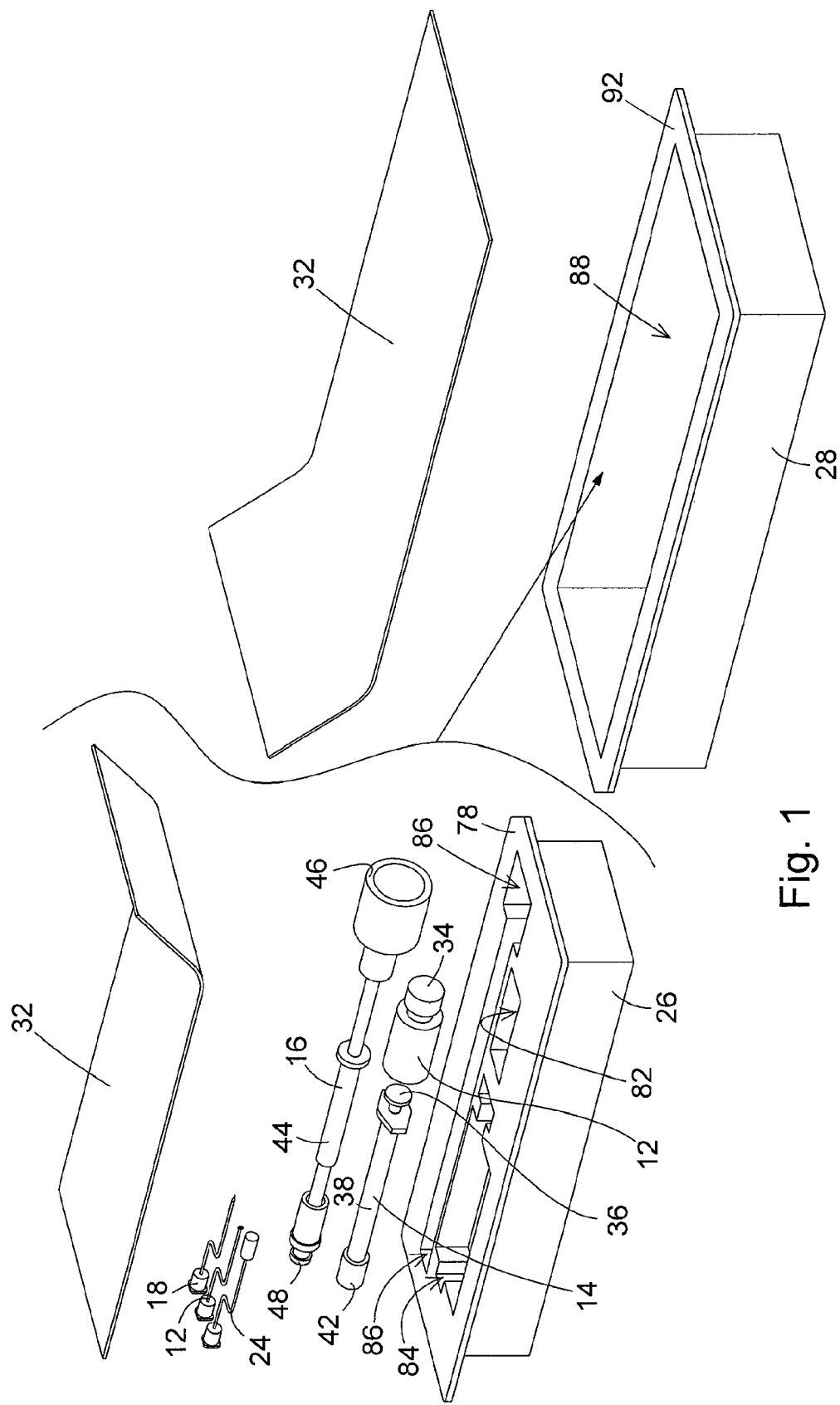
FIG. 1 is a perspective view of the component parts of the apparatus of the invention and of the packaging that combines the component parts as a kit in the packaging.

The component parts of the apparatus of the invention are shown in FIG. 1. These include the parts of the invention that enable the safe application of a pharmaceutical such as mitomycin-C to the tympanic membrane, or ear drum, in an ear canal, and the assembling of the component parts after their use for safe disposal. Several of the component parts are known in the prior art in one form or another. Therefore, these component parts will be referred to by their commonly understood names, but will not be described in detail. The materials used to construct the component parts of the invention are those that are most typically used for constructing similar parts.

The component parts include a vial 12 of the pharmaceutical, a syringe 14, a diluent carrier 16, a plurality of ear needles 18, 22, 24, a resilient packaging block 26, a semi-rigid packaging box 28, and a sheet of packaging material 32. As stated earlier, each of these component parts is constructed of materials typically used in manufacturing similar parts.

The pharmaceutical vial 12 has a construction that is known in the art. In the preferred embodiment, the pharmaceutical contained by the vial 12 is a single dose of an otologic formulation of mitomycin-C. The mitomycin-C has a specific color. In its natural state, mitomycin is purple. Like conventional pharmaceutical vials, the vial 12 has a top 34 that can be pierced by a syringe needle which seals closed after the needle is removed from the top 34.

The syringe 14 has the typical construction of a syringe. A plunger 36 extends from a proximal end of the syringe body 38, and the opposite distal end 42 of the syringe body is provided with a female luer. The operation of the syringe 14 is conventional.

The diluent carrier 16 in the preferred embodiment of the invention is comprised of a second syringe 44 containing a sterile liquid such as water, and a one-way valve 46, for example a Qosina-brand valve. However, other types of diluent carriers that perform the same function as the diluent carrier 16 to be described could be used in the apparatus kit. In the preferred embodiment, the diluent carrier 16 contains sterilized water. The amount of water provided in the carrier 16 is determined to mix with the pharmaceutical contained in the vial 12 to reconstitute the pharmaceutical in the carrier 16. The carrier 16 has a proximal end 46 that is adapted to receive the vial top 34. A needle (not shown) is positioned in the carrier proximal end 46 to pierce the vial top 34 and communicate the pharmaceutical contained by the vial 12 with the water contained in the carrier 16. The carrier distal end 48 is adapted to communicate with the female luer at the syringe distal end 42. This enables the syringe 14 to withdraw the reconstituted pharmaceutical from the carrier 16 into the body 38 of the syringe. As stated earlier, diluent carriers of this type are known in the art.

Each of the ear needles 18, 22, 24 have the same basic construction, the exception being the shape of the absorbent pad fixed to the needle. Each needle 18, 22, 24 is formed from a length of 20 gauge hypodermic tubing 52 with opposite proximal 54 and distal 56 ends. An intermediate portion 58 of the tubing is formed with pairs of right angles to adapt the tubing 52 for insertion into the ear canal. A standard syringe male luer 62 is secured to each needle proximal end 54. The male luer 62 is adapted to attach to the female luer 42 at the syringe distal end to communicate the needle tubing 52 with the syringe body 38.

The three ear needles 18, 22, 24 differ from each other in that they have different shaped absorbent pads 68, 72, 74 at the distal ends of the needles. In the preferred embodiment, each of the absorbent pads 68, 72, 74 is fixed to the distal ends of each of the needles 18, 22, 24. In the preferred embodiment, the pads 68, 72, 74 are constructed of an absorbent material that is known in the art and is used for the transient application of a pharmaceutical such as mitomycin-C. Each of the absorbent pads 68, 72, 74 is preferably constructed of polyvinyl acetate (PVA) sponge material. This material rapidly absorbs liquid such as the mitomycin-C. The dimensions of each pad 68, 72, 74 hold a specific volume of the mitomycin-C that enables a therapeutic, single dose of the otologic formulation of mitomycin-C to be applied to the tympanic membrane of an ear.

One of the absorbent pads 68 has a cone shape that projects from the needle distal end 56 to a tip of the cone. The cone shape of the pad 68 has a center axis 76 that is coaxial with a center axis 76 of the needle distal end 56. In the preferred embodiment, the cone-shaped pad 68 has a base diameter dimension of 0.04", and an axial length dimension of 0.12".

Another of the absorbent pads 72 has a planar configuration that extends transverse to the center axis 76 of the needle distal end 56. This pad 72 is formed in a general kidney shape. The pad 72 has a length dimension of 0.08", and a width dimension of 0.04". The pad 72 has a thickness of 0.02".

A third pad 74 has a cylindrical configuration. The center axis of the pad cylinder 74 is coaxial with the center axis 76 of the needle distal end 56. In this embodiment of the pad 74, the pad has a diameter dimension of 0.2" and an axial length dimension of 0.4".

Each of the above-described component parts of the apparatus is contained in the packaging of the apparatus that includes the box 28, the resilient block 26, and the sheet of packaging material 32. Each of these packaging component parts is constructed of materials used in the safe storage, transport, and disposal of pharmaceuticals and instruments used with pharmaceuticals such as mitomycin-C.

The block 28 is constructed of a resilient material such as foam rubber. The block 28 has a top surface 78 that is formed with a plurality of cavities or compartments 82, 84, 86. Each of the compartments 82, 84, 86 is dimensioned to receive and securely hold the vial 12, the syringe 14, the diluent carrier 16, and the plurality of ear needles 18, 22, 24. The compartments 82, 84, 86 securely hold the component parts of the apparatus and provide cushioning of the component parts to protect the parts during their storage and transportation.

The box 28 is dimensioned with an interior 88 that receives the resilient block 26 and securely holds the block 26 in the box interior. The box has top edges 92 that border the top opening to the box interior 88. The box 28 is dimensioned so that the top edges 92 will be positioned in the same plane as the top surface 78 of the resilient block 26 when the block is positioned in the box interior 88.

The sheet of packaging material 32 can be any type of material currently used to provide a sealed enclosure of the box 28. The packaging material 32 can be shrink-wrap applied around the box 28, or can be a resealable sheet of packaging material that can be peeled back from the box top edges 92 and then resealed to the top edges after the component parts of the apparatus have been removed from the packaging and used.

In use of the apparatus of the invention according to the method of the invention, the packaging is first opened by removing the sheet material 32 from the top edges 92 of the box. This exposes the block compartments 82, 84, 86 in the block top surfaces 78. The vial 12, the syringe 14, the diluent carrier 16, and the ear needles 18, 22, 24 may be removed from their respective compartments in the resilient block 26.

The vial 12 of pharmaceutical, preferably mitomycin-C having a specific color, is then connected to the diluent carrier proximal end 46. This communicates the pharmaceutical in the vial 12 with the interior of the carrier 16. The pharmaceutical mixes with the water in the carrier 16, reconstituting the mitomycin-C. In addition, a viscous agent and/or an adhesive agent may be mixed with the mitomycin-C in the carrier 16. The carrier distal end 48 is then connected to the syringe distal end 42. This communicates the reconstituted pharmaceutical in the interior of the carrier 16 with the interior of the syringe body 38.

Withdrawing the syringe plunger 36 from the syringe body 38 creates a suction in the syringe that draws the reconstituted pharmaceutical from the carrier 16 into the syringe body.

After the pharmaceutical has been drawn into the syringe body 38, the syringe 14 is disconnected from the diluent carrier 16.

A selected one of the ear needles 18, 22, 24 is next connected to the syringe distal end 42. The choice of the ear needle 18, 22, 24 is made by the physician determining which configuration of absorbent pad 68, 72, 74 is desirable for applying the mitomycin-C to the tympanic membrane of the patient. With the desired ear needle 18, 22, 24 secured to the syringe distal end 42, the syringe is prepared for application of the pharmaceutical to the tympanic membrane.

Application of the mitomycin-C to the tympanic membrane is illustrated in FIGS. 7-11. FIG. 7 shows a cross-section representation of the inner ear canal 94 and the tympanic membrane 96 or ear drum in the ear canal. FIG. 8 shows an enlarged view of the portion of the ear canals 94 shown in the rectangular box of FIG. 7. In FIG. 8, a fluid buildup 98 on one side of the ear drum 96 is a source of infection in the ear that is removed by the method of the invention.

FIG. 9 illustrates the application of the mitomycin-C to the tympanic membrane of the ear drum 96 by use of the absorbent pad 68 having the cone-shaped configuration. This pad 68 can be used to paint a location on the surface of the tympanic membrane 96 with the mitomycin-C absorbed in the pad 68.

FIG. 10 illustrates the application of the mitomycin-C to a location on the tympanic membrane 96 using the planar, kidney-shaped configuration 72 of the absorbent pad. This configuration of the absorbent pad 72 can be used to stamp a location of application of the mitomycin-C on the tympanic membrane 96.

FIG. 11 illustrates the cylindrical-shaped absorbent pad 74 being used to appy the mitomycin-C to a location in the ear canal. The cylindrical-shaped pad 74 is used to apply the mitomycin-C to the circumference of the ear canal.

Each of the absorbent pads 68, 72, 74 enables an application of a single dose of an otologic formulation of mitomycin-C to the tympanic membrane 96. Suspending a viscous agent or an adhesive agent in the mitomycin-C enables the mitomycin-C to remain in situ on the tympanic membrane 96 and cause anti-metabolic activity on the membrane that is localized and defined by the specific color of the mitomycin-C, which is naturally purple.

A laser 102 that emits a laser beam 104 that is specifically tuned to the color of the mitomycin-C applied to the tympanic membrane 96 may then be used to ablate the tympanic membrane tissue at a location defined by the specific color of the mitomycin-C applied to the tissue. The application of the specifically tuned laser beam 104 to the tympanic membrane 96 is illustrated in FIG. 12. The laser beam 104 emitted from the laser 102 produces a photodynamic, selective, laser myringotomy 106. The effects of the mitomycin-C applied to the tympanic membrane 96 result in a sustained patency of the myringotomy 106 opening, produced by the laser beam 104.

Thus, the apparatus of the invention and its method of use discussed above enable a safe and simplified photodynamic laser myringotomy procedure that is not invasive and accommodates the non-compliant child patient population.

The apparatus of the invention and its method of use have been described above by reference to specific embodiments of the invention. It should be understood that modifications and variations could be made to the invention described without departing from the intended scope of the following claims.

The invention claims is:

1. An apparatus for application of a pharmaceutical and performing a selective photodynamic laser myringotomy, the apparatus comprising:

the pharmaceutical being a single dose of an otologic formulation of mitomycin-C, the single dose of mitomycin-C having a predetermined specific color; and,
a laser that is specifically tuned to emit a laser beam having a wavelength that is absorbed at a location defined by the specific color of the single dose of mitomycin-C.

2. The apparatus of claim 1, further comprising:
the single dose of mitomycin-C being suspended in an agent that permeates living tissue with the mitomycin-C.

3. The apparatus of claim 1, further comprising:
the single dose of mitomycin-C being suspended in a viscous agent.

4. The apparatus of claim 1, further comprising:
the single dose of mitomycin-C being suspended in an adhesive agent.

5. The apparatus of claim 1, further comprising:
an ear needle that is adapted for receiving the single dose of mitomycin-C and delivering the mitomycin-C to a tympanic membrane to remain in situ on the tympanic membrane and cause anti-metabolic activity on the tympanic membrane.

6. The apparatus of claim 5, further comprising:
the ear needle having a tubular length with opposite proximal and distal ends, the needle proximal end being adapted for communicating the needle with a syringe, and the needle distal end having an absorbent pad fixed to the distal end, the pad being dimensioned to absorb and hold the single dose of mitomycin-C and apply the single dose of mitomycin-C to a tympanic membrane of an ear.

7. The apparatus of claim 6, further comprising:
the pad having a cone shape projecting from the needle distal end to a tip of the cone shape.

8. The apparatus of claim 6, further comprising:
the pad having a cylindrical shape that projects from the needle distal end.

9. The apparatus of claim 6, further comprising:
the needle distal end having a center axis; and,
the pad being planar and being positioned transverse to the needle distal end center axis.

10. The apparatus of claim 1, further comprising:
a plurality of ear needles that are each adapted for receiving the single dose of mitomycin-C, each needle having a tubular length with opposite proximal and distal ends, each needle proximal end being adapted for communicating the needle with a syringe; and,
a plurality of absorbent pads fixed to the distal end of the plurality of needles, at least some of the plurality of absorbent pads having different shapes.

11. The apparatus of claim 10, further comprising:
a tray;
a lid positionable over the tray;
the plurality of needles being positioned in the tray and covered by the lid;
a container of the single dose of mitomycin-C positioned in the tray and covered by the lid; and,
a syringe positioned in the tray and covered by the lid.

12. The apparatus of claim 11, further comprising:
the tray having a plurality of separated compartments;
the plurality of ear needles being positioned in a compartment of the tray;
the container being positioned in a compartment of the tray; and,
the syringe being positioned in a compartment of the tray.

13. The apparatus of claim 11, further comprising:
a diluent carrier positioned in a compartment of the tray.

14. An apparatus for application of a pharmaceutical comprising:
the pharmaceutical being a single dose of an otologic formulation of mitomycin-C;
the single dose of mitomycin-C having a specific color;
an ear needle that is adapted for receiving the single dose of mitomycin-C and delivering the mitomycin-C to a tympanic membrane to remain in situ on the tympanic membrane and cause anti-metabolic activity on the tympanic membrane that is localized and defined by the specific color; and,
a laser that is specifically tuned to emit a laser beam that will ablate tympanic membrane tissue at a location on the tympanic membrane that is defined by the specific color and will not effect adjacent structure of a dissimilar color.

15. A method for application of a pharmaceutical and performing selective a photodynamic laser myringotomy, the method comprising:
providing a single dose of an otologic formulation of mitomycin-C; coloring the single dose of mitomycin-C with a predetermined specific color;
applying the single dose of mitomycin-C to interior tissue of an ear canal; and,
ablating the tissue at a location on the tissue to which the mitomycin-C has been applied with a laser beam having a wavelength that is absorbed by the specific color of the mitomycin-C, while being ignored by adjacent structures of a dissimilar color.

16. The method of claim 15, further comprising:
applying the mitomycin-C to a tympanic membrane in the ear canal.

17. The method of claim 15, further comprising:
suspending the mitomycin-C in a viscous agent.

18. The method of claim 15, further comprising:
suspending the mitomycin-C in an adhesive agent that can permeate living tissue.

19. A method for application of a pharmaceutical and performing a selective photodynamic laser myringotomy comprising:
providing a single dose of an otologic formulation of mitomycin-C;
applying the single dose of mitomycin-C to interior tissue of an ear canal;
giving the mitomycin-C a specific color;
applying the mitomycin-C to a tympanic membrane in the ear canal;
causing anti-metabolic activity on the tympanic membrane by application of the mitomycin-C at a location on the tympanic membrane that is defined by the color of the mitomycin-C; and,
treating the location on the tympanic membrane by ablating the location with a laser beam specifically tuned to the color of the mitomycin-C.

* * * * *